United States Patent [19]

Stokes et al.

[11] Patent Number: 5,180,606
[45] Date of Patent: * Jan. 19, 1993

[54] APPARATUS FOR APPLYING A CONTROLLED AMOUNT OF REAGENT TO A MICROSCOPE SLIDE OR THE LIKE

[75] Inventors: Barry O. Stokes, Logan; Gary D. Bradshaw, Wellsville; Wayne K. Barlow, Providence, all of Utah

[73] Assignee: Wescor, Inc., Logan, Utah

[ * ] Notice: The portion of the term of this patent subsequent to Apr. 23, 2008 has been disclaimed.

[21] Appl. No.: 690,781

[22] Filed: Apr. 23, 1991

Related U.S. Application Data

[63] Continuation-in-part of Ser. No. 350,106, May 9, 1989, Pat. No. 5,009,185.

[51] Int. Cl.$^5$ ............................................. B05D 1/02
[52] U.S. Cl. ......................................... 427/2; 118/52; 118/314; 427/240; 427/425
[58] Field of Search .................. 118/240, 425, 52, 320, 118/314; 427/2

[56] References Cited

U.S. PATENT DOCUMENTS

| | | | |
|---|---|---|---|
| 2,848,353 | 8/1958 | Norris | 117/102 |
| 4,004,550 | 1/1977 | White et al. | 118/134 |
| 4,084,615 | 4/1978 | Klein et al. | 137/624.11 |
| 4,089,989 | 5/1978 | White et al. | 427/2 |
| 5,009,185 | 4/1991 | Stokes et al. | 118/52 |

OTHER PUBLICATIONS

SIGMA Brochure describing Sigma 4-10 and Sigma 4K10 centrifuge equipment by B. Braun Diessel Biotech GmbH, Melsungen, Germany.

*Primary Examiner*—Bernard Nozick
*Attorney, Agent, or Firm*—Mallinckrodt & Mallinckrodt

[57] ABSTRACT

Apparatus for applying a controlled amount of reagent to one or more miscroscope slide or the like includes a spray chamber and a carousel adapted to hold a plurality of slides and to be mounted for rotation in the spray chamber. Nozzles are mounted to spray reagent onto the slides in the carousel as they rotate by the nozzles. Accurate control of the time or angular rotation during which the reagent is sprayed from the nozzles is obtained by placing a control valve in the flow line between a reagent pump and the nozzle and operating the valve to control flow of reagent. Control circuitry determines the position of the slides and carousel in the spray chamber and coordinates operation of the pumps, valves, and rotation of the carousel to accurately cause spray of reagent onto the slides. The slide holding carousel may be replaced by an interchangable centrifuge rotor when it is desired to perform cytocentrifuging tests.

15 Claims, 6 Drawing Sheets

APPARATUS FOR APPLYING A CONTROLLED AMOUNT OF REAGENT TO A MICROSCOPE SLIDE OR THE LIKE

This is a continuation-in-part of application Ser. No. 350,106, filed May 9, 1989, entitled *Apparatus for Applying a Controlled Amount of Reagent to a Microscope Slide or the Like*, now U.S. Pat. No. 5,009,185.

BACKGROUND OF THE INVENTION

1. Field

The invention is in the field of automated equipment for staining specimens on glass slides, for performing cytocentrifuging operations, or for performing other operations that require rotation of a carousel or rotor.

2. State of the Art

There are currently many medical diagnostic tests performed by applying a biological material, such as blood, pus, urine, cervical smears, cytology or histology specimens, or a bacterial culture, on a glass slide, such as a microscope slide, by smearing the material onto the slide, and then evaluating the material applied to the slide. In most instances, the smear will be treated with some type of reagent, such as a stain, to bring out or make visible various features of the smear not otherwise visible. In most cases the smear will also be fixed to the slide prior to or concurrently with staining.

It is currently normal practice with hematology smears, i.e. blood smears, to place a smear on a slide and allow the smear to dry. The smear is then fixed on the slide by wetting the smear wtih anhydrous methanol and allowing the methanol to evaporate or dry. Cytology specimens are fixed wet wtih spray fixatives such as alcohol with polyethelene glycol. Dye is then applied to the smear to bring out desired characteristics of the smear and the smear is then examined. While the staining intensity achieved depends on the time and the amount of stain applied, considerable variation in those variables still yield satisfactory results.

In addition to blood smear staining, it is common to observe bacteria in specimens and products as an indication of infection or contamination. Material to be observed is usually applied to a microscope slide, generally by smearing the material on the slide, fixed, and stained using the well-known gram staining procedure. The gram staining consists of saturation of the smear wtih crystal violet followed by a thorough water wash, and then saturation wtih iodine followed by a thorough water wash. These steps are non-critical and as long as enough crystal violet and iodine are used to saturate the smear, any extra amount used does not affect the results obtained. The critical step in gram staining is decolorization. This is done by applying an organic solvent to selectively remove the crystal violet-iodine complex from the gram negative, but not the gram positive organisms. A counterstain containing safranin is then applied to stain the gram negative organisms red.

The rate of removal of the complex is species specific. If too little decolorizer is added, the gram negative organisms (red) will appear gram positive (blue). If too much is added, the gram positive organisms will appear gram negative. Reliable decolorization can only be achieved where the amount of solvent applied to the smear is accurately controlled.

U.S. Pat. Nos. 4,004,550 and 4,089,989 show an automated slide stainer which automatically applies stain to slides mounted on a carousel for rotation in a staining chamber. A commercial version of the stainer shown in such patents is manufactured by Wescor, Inc., Loga, Utah and sold under the trademark Aerospray.

In the commercial version of the stainer shown in the above cited patents, slides to be stained are placed in a slide holding carousel which is rotated by a motor, as shown in the patent. During rotation of the carousel, the slides are sprayed with various reagents as they move past a spray nozzle, again as shown in the patents. However, it is impractical to use aerosol cans, as shown in the patents, for spraying the various reagents. Rather, pumps are provided for each of the reagents to pump the reagents from their container or other reservoir through a check valve to prevent back flow and through a nozzle which atomizes the reagent and sprays it onto the slides in the spray chamber. In order to spray a reagent onto the slide, the pump for the appropriate reagent is energized. The reagent is then sprayed into the chamber and onto the slides during the time its pump is energized. The pumps are timed and controlled to pump the proper reagents into the spray chamber at the proper times and for the proper length of time. With such system, however, the spray continues to flow into the chamber for 1 to 1.5 seconds during wind-down of the pump and depressurization of the delivery line after power to the pump is cutoff. This prevents highly accurate application of a reagent to the slides. Of the slide carousel rotates at 30 RPM, an additional one second of spray application during wind down of the pump will give half of the slides in the carousel an extra application of reagent. Furthermore, the application of reagent to the slides is not uniform as the pump loses pressure. This means that some of the slides will receive an extra application of reagent and some of the slides will receive uneven dribble. In the case of hematology staining, as indicated above, this unevenness does not seem to be a significant problem. The staining approaches a saturation point and differences in staining due to this uneven application are not detectable. However, in gram staining, the application of the decolorization solvent must be accurately controlled and the extra application of such solvent to some of the slides and not others affects the accuracy and reproducibility of the gram staining results. Thus, the currently commercially available automated staining equipment made according to the referenced patents cannot be used for optimal gram staining.

In addition to the problem encountered if such equipment is used for gram staining, the additional stain used during wind down of the pump wastes the various reagents used. Further, because of the wind down time, it has not been practical to try to program the equipment for use with less than a full load of slides. Thus, the equipment is set to provide full pressure spray for the appropriate number of full revolutions of the carousel, regardless of how many slides are actually in the carousel. If the carousel is built to hold twelve slides, and only one or two slides are to be treated, the equipment will still spray enough reagent into the spray chamber to treat twelve slides, thus additionally wasting reagent.

There are also some tests that do not involve staining but require centrifuging of a sample. Such tests currently utilize their own specialized centrifuging equipment. However, the staining equipment utilizing a rotating carousel therein could be used for centrifuging if the carousel was changed to an appropriate centrifuge rotor. Therefore, the same basic equipment could be used for several types of tests if carousels and centrifuging rotors were interchangeable.

SUMMARY OF THE INVENTION

According to the invention, apparatus for applying a controlled amount of reagent to a slide or the like having a specimen thereon includes a spray chamber and carousel means adapted to hold a plurality of slides and to be mounted for rotation in the spray chamber. Means is provided for rotating the carousel means in the spray chamber and nozzle means are mounted in the spray chamber for directing spray of reagent toward the carousel means. Reagent to be applied to the slides is stored in a reagent reservoir and pump means pumps the reagents from the reservoir through a flow line to the nozzle when it is desired to spray the reagent on the slides. Accurate control of the time during which the reagent is sprayed from the nozzle is obtained by placing a remotely operated valve in the flow line between the pump and the nozzle, energizing the pump in anticipation of providing fluid to the nozzle, and operating the valve to control the flow of fluid to the nozzle during the time the pump is energized. This also involves either substantially eliminating any compressible material, such as air pockets or expandable tubing in the line between the valve and the nozzle which would cause continued spray of reagent through the nozzle after closing of the valve, or venting the flow line between the valve and nozzle immediately upon closing the valve to release any pressure in the flow line caused by air pockets or expandable material therein to prevent continued spray of reagent after the valve is closed. Control means, such as a microprocessor and related circuitry, coordinates operation of the pump, valve, and carousel to accurately cause spray of reagent during known passage of the carousel past the nozzle.

Means may be provided to sense the angular position of the carousel within the spray chamber and thereby determine the positions of the slides in the chamber for application of reagent to those slides without the waste of reagent occasioned by continuous spraying as a partially full carousel is rotated in the chamber. Such means may advantageously take the form of magnets mounted on the carousel and a sensor mounted on the spray chamber to sense passage of a magnet. A motor encoder provides signals representative of the rotation of the motor shaft. Using the position signals generated by the magnets, along with the encoder signals, accurate control of the device is achieved. Control of many functions of the device may be accomplished using only the motor encoder. Rather than using sensors to determine the angular position of the carousel, sensors that can sense the presence of individual slides could be used.

The apparatus of the invention can be used for carrying out procedures other than staining, such as centrifuging wherein a centrifuge rotor is substituted for the slide carousel in the spray chamber. Various rotation cycles and speeds can be used wtih such rotors. During centrifuging, no spraying is done and sensors, such as the magnetic sensors described, upon not sensing passage of magnets, may be used to ensure that spraying is not done during centrifuging. Sensors may also be used to automatically identify whether a slide carousel, centrifuging rotor, or other rotor is in position in the spray chamber.

THE DRAWINGS

In the accompanying drawings, which show the best mode presently contemplated for carrying out the invention.

DETAILED DESCRIPTION OF THE ILLUSTRATED EMBODIMENTS

Figure 1:
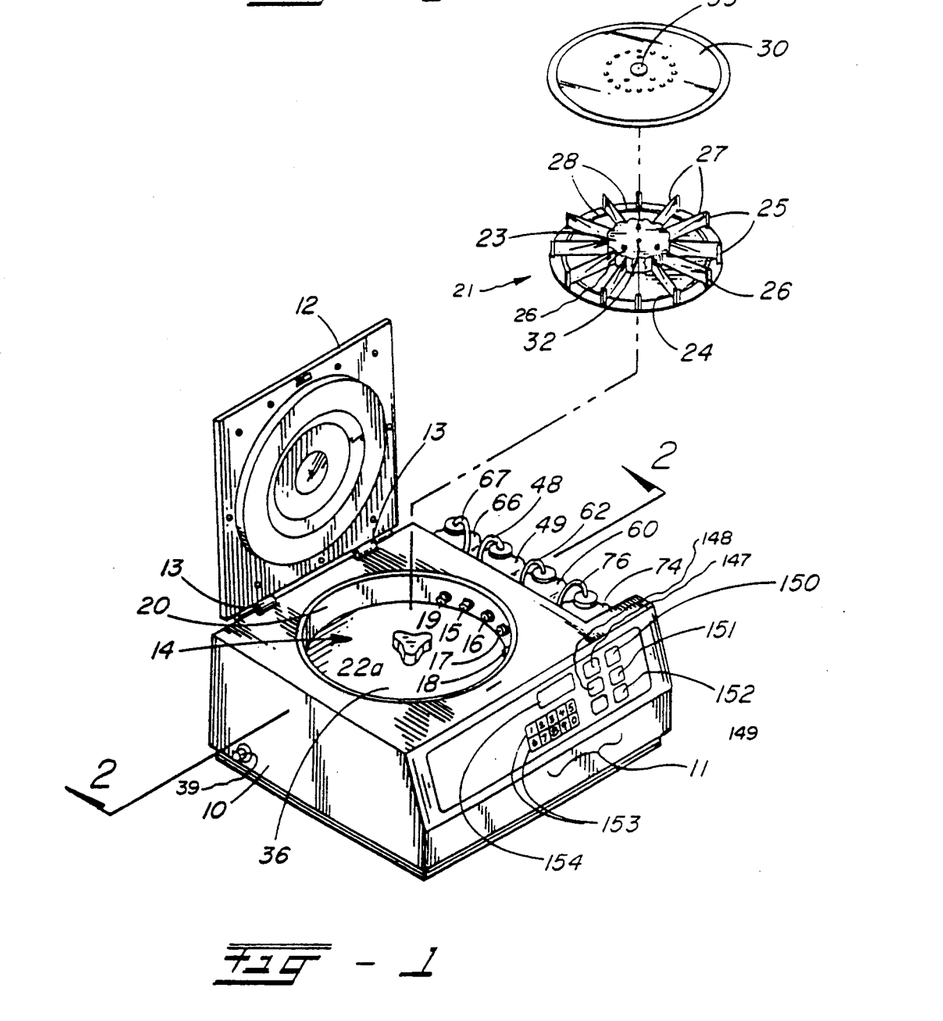
FIG. 1, is a perspective view of an apparatus of the invention.
Figure 2:
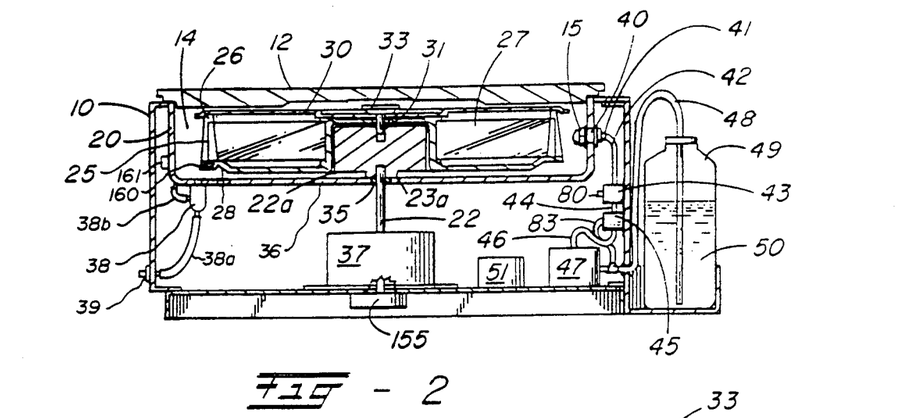
FIG. 2, a vertical section taken on the line 2—2 of FIG. 1 showing some of the internal components schematically.

A device which can be used for automatic slide staining or for centrifuging with a different, interchangeable centrifuging rotor, is shown in FIGS. 1 and 2 and includes an outer housing 10 which encloses the operating components of the equipment and has a control panel 11 thereon easily accessible to a user of the equipment. A top cover 12 is hingedly mounted on top of housing 10 as at 13 and opens to expose a spray chamber 14. Spray nozzles 15, 16, 17, 18, and 19 are arranged about a portion of the outside wall 20 of spray chamber 14.

For slide staining, a carousel 21 is adapted to fit into spray chamber 14 over a receiving hub 22a secured to the end of shaft 22 and is adapted to be rotated in the spray chamber 14 by shaft 22. Carousel 21 has a central hub portion 23, a bottom portion 24 extending outwardly from hub 23, and upstanding slide end holders 25 extending from bottom portion 24 and preferably spaced evenly about the circumference thereof. Hub 23 and slide end holders 25 have slots 26 therein to receive the ends of microscope slides 27 which can be placed to extend between the hub 23 and a slide end holder 25. It is preferred that carousel 21 be provided with at least twelve slide end holders 25 so that up to twelve individual slides can be mounted in the carousel, preferably in balanced configuration about the carousel. The bottom portion of the carousel forms a collecting area for reagent which can run out of the collecting area through circumferentially placed slots 28. A carousel cover 30 fits over the top of the carousel 21 and is held in place by a bayonet latching mechanism 31 which engages with a receiving hole 32 in carousel hub 23 and has an enlarged head 33 which allows the engaging mechanism to be easily secured to or removed from the hub and serves as a handle for holding and loading the carousel into spray chamber 14.

Shaft 22 extends through a seal 35 in spray chamber bottom 36 and is coupled for rotation to motor 37, shown schematically in FIG. 2. Thus, operation of motor 37 causes rotation of shaft 22 and receiving hub 22a secured to the end thereof which, in turn, causes rotation of carousel 21 when mounted thereon in spray chamber 14.

In operation of the apparatus, the motor is operated to rotate the carousel at a known rate and reagent to be applied to the slides in the carousel sprayed through one or more of the nozzles into the spray chamber. As the carousel rotates, with each rotation of the carousel, each of the slides pass by the nozzles and the reagent sprayed from the nozzles is applied to the slides as they pass by. By controlling the speed at which the carousel rotates and timing the spray of reagent from the nozzles, a desired amount of reagent can be applied to the slides. While five nozzles have been shown in the spray chamber of FIG. 1, and this is preferred for use in gram staining where three of the nozzles are used for the reagent, each nozzle supplying a different reagent at a different time, and two of the nozzles are used to supply a wash fluid, any number of nozzles, more or less, may be used and a single nozzle could be used to supply different reagents at different times.

Spray chamber 14 is preferably provided with a drain fitting 38, to which drain tubing 38a is attached and extends to drain fitting 39 mounted in housing 10. Drain fitting 38 also includes a vent connection to which vent tubing 38b is attached. Tubing 38b extends through the back wall of the apparatus to provide a vent to the atmosphere for the drain. Spray chamber bottom 36 could be sloped or otherwise shaped to encourage flow of reagent collecting in the chamber to drain 38.

As shown schematically in FIG. 2, nozzle 15 is mounted in a nozzle holder 40 with a tubing connector 41 extending therefrom. Tubing 42 extends from connector 41 to a remotely operated wash valve 43. Tubing 44 extends from wash valve 43 to a remotely operated control valve 45. Tubing 46 extends from control valve 45 to the output side of pump 47. The inlet side of pump 47 is connected through tubing 48 to a source of reagent, such as a bottle 49 containing a reagent 50.

In the equipment that has been manufactured and sold under U.S. Pat. Nos. 4,004,550 and 4,089,989 as mentioned in the Sate of the Art Section of this application, tubing extends directly from pump 47 to normally open wash valve 43 with tubing then extending to nozzle holder hose connector 41. Control valve 45 has not been used with such equipment. Without the control valve, when it is desired to spray reagent onto the slides in the carousel rotating in the spray chamber, pump 47 is energized by a timing and control means 51 and reagent is drawn by pump 47 from container 49 and supplied through the open wash valve directly to nozzle 15. This results in the problems previously mentioned that spray continues for a short time after the pump is deenergized while the pump winds down.

With the arrangement of the invention where the spray of the reagent into the spray chamber 14 has to be accurately controlled, the remotely-controlled control valve 45 is placed in the flow line between the pump and the nozzle to more accurately control the flow from the pump to the nozzle.

Figure 3:
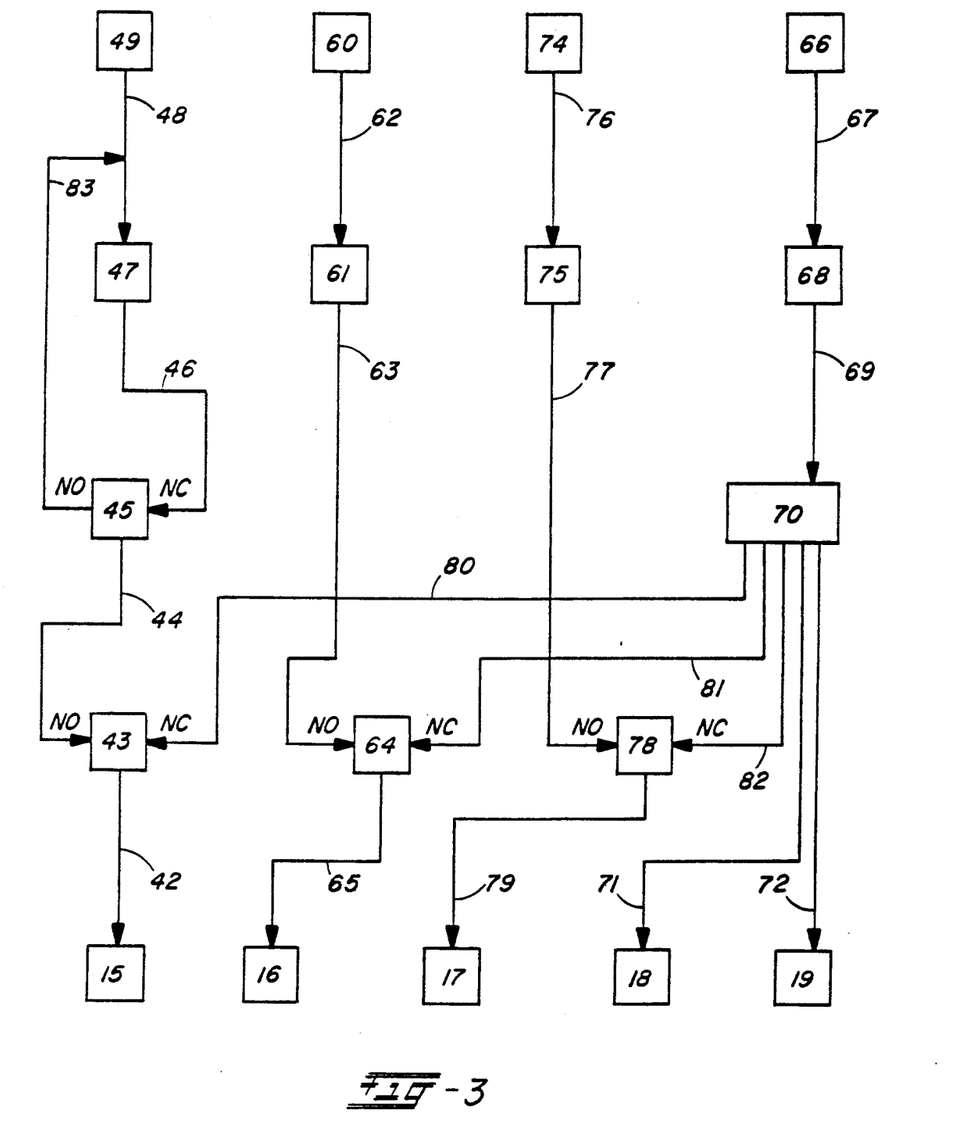
FIG. 3, a flow diagram showing flow of reagent in the apparatus.

In the particular embodiment of FIGS. 2 and 3, control valve 45 is provided between the pump and wash valve 43. Valve 45 controls flow of reagent from the pump to the nozzle. Wash valve 43 is provided to allow flow of a wash solution, such as water or alcohol, through the nozzle prior to ceasing operation of the apparatus for a period of time, such as overnight. Operation of valve 43 will be explained in more detail later. With gram staining, only the flow of the decolorization and counterstaining reagent is critical to control so it is only necessary to provide a flow control valve in the line for one of the nozzles. The remaining nozzles do not require critical control of the reagent pumped to the nozzles, so flow control valves are not necessary in the other lines. However, such flow control valves are preferred and are necessary if the apparatus is to be operated to conserve all reagents by controlling the spray of reagent to spray only during the time the slides present in the carousel are passing the spray nozzles when less than a full load of slides is being stained.

FIG. 3 shows a flow diagram for the five nozzles provided in the apparatus of FIG. 1. The operation of the apparatus will be described specifically for gram staining.

Slides having bacterial specimens thereon are placed in the carousel and the carousel is positioned on receiving hub 22a in spray chamber 14. Prior to placing the slides in the carousel, the bacterial specimens generally will have been fixed to the slides in normal manner, such as by heating or by an application of methanol. Top 12 is closed over the spray chamber. The operator then selects the desired operations and starts operation of the apparatus by means of controls on control panel 11.

Upon the initiation of operation of the apparatus, control means 51 energizes motor 37 to cause rotation of the carousel. The carousel is operated at a known rate of rotation, for example, thirty RPM, for the spraying operation. The first step in gram staining is saturation of the smear with crystal violet. Crystal violet is provided in one of the reagent reservoirs, such as bottle 60, FIGS. 1 and 3. Pump 31, FIG. 3, is energized to draw the crystal violet from reservoir 60 to pump 61 through tubing 62. The crystal violet is pumped through tubing 63 to the normally open inlet of wash valve 64, FIG. 3, through open valve 64 and tubing 65 to nozzle 16. The control means 51 energizes pump 61 to start flow of crystal violet and continues operation of pump 61 for a set number of full revolutions of the carousel to saturate the specimens on the slides with crystal violet. It has been found that a ten second spray time (five full revolutions of the carousel) is generally satisfactory. After the set number of revolutions, pump 61 is deenergized and spray continues during wind down of the pump. However, since this spray is a saturation operation, the extra spray during wind down of the pump does not affect the results.

After application of the crystal violet, it has been found beneficial to increase the speed of rotation of the carousel to between 500 to 1000 RPM for three seconds to remove the excess crystal violet reagent from the slides. The rotation speed is then returned to thirty RPM and a water wash is provided for ten to sixteen seconds. It usually requires about sixteen seconds to slow the carousel down to thirty RPM from the high speed spin cycle and to be sure that the speed has stabilized at the lower speed.

For the water wash, water is provided in bottle 66 which is drawn through tubing 67 to the inlet of pump 68, FIG. 3. Pump 68 then pumps the water through tubing 69 to manifold 70, FIG. 3, through tubing 71 and 72, FIG. 3, to nozzles 18 and 19, FIG. 1. Nozzle 18 is mounted in spray chamber 14 similarly to nozzles 15, 16, and 17 to provide spray to the front surface of the slides, i.e. the surface wtih the specimens thereon, as they pass the nozzle. Nozzle 19, however, is arranged to spray the back side of the slides as they pass.

After saturation with crystal violet and the subsequent water wash, the next step is to saturate the specimens with iodine. The iodine is supplied in bottle 74. Pump 75, FIG. 3, is energized to draw iodine from bottle 74 through tubing 76 to the inlet of pump 75. The iodine reagent then flows from the output of pump 75 through tubing 77, FIG. 3, normally open wash valve 78, tubing 79, to nozzle 17. The pump is operated by control means 51 similarly to pump 64 to saturate the specimens with iodine. Ten seconds of iodine spray has been found satisfactory.

After application of the iodine, the speed of the carousel is increased for a three second high speed cycle (500–100 RPM), followed by a return to the thirty RPM speed and a twelve to sixteen second water wash.

After saturation with iodine and the subsequent water wash, the next steps in gram staining are the critical steps of decolorization and counterstaining. With the apparatus of the invention, the decolorization solvent and the counterstain safranin are mixed together and applied together in a single spray step. This step requires the accurate application of the organic solvent containing the red counterstain safranin to the slides. The decolorization solvent and counterstain solution 50, FIG. 2, is supplied in bottle 49. Pump 47 draws the counterstain solvent from bottle 49 through tubing 48 to the pump and then pumps it through tubing 46 to normally closed valve 45. In order to provide accurate control of the spray of the counterstain solvent, pump 47 is energized by control means 51 one second prior to the time spraying is to start. This allows the pressure in pump 47 and line 46 from the pump to build up and stabilize. When spraying is to start, control means 51 causes operation of valve 45 to open the normally closed inlet of the valve so that counterstain solvent flows through the valve, through tubing 44, through normally open valve 43, and through tubing 42 to nozzle 15. Tubings 42 and 44 are arranged so that they remain full of fluid between operations, so that with the pressure from the pump stabilized prior to opening valve 45, spray of the solvent through nozzle 15 begins immediately upon opening valve 45. Upon initially opening valve 45, control means 51 keeps valve 45 open to allow two complete revolutions of the carousel. Thus, each slide in the carousel passes by the spray nozzle twice. With a rotation rate of thirty RPM, each complete rotation takes two seconds, so the initial spray is timed to continue for four seconds. At the end of four seconds, control means 51 causes valve 45 to close. This immediately causes the spray through nozzle 15 to cease.

Since the counterstain solvent must be absorbed into the specimen to work and decolorization and counterstaining do not occur immediately, it is usually necessary to apply the counterstain solvent, allow some time for it to be absorbed into the specimens, apply some more counterstain solvent, allow time for it to be absorbed, and continue to intermittent application of counterstain solvent with absorption periods until the desired decolorization and counterstaining takes place. Because the desired amount of decolorization and counterstaining varies form user to user and because the thickness of the specimens and thus the amount of counterstain solvent required for a given specimen or batch of specimens will vary, it will usually be advantageous to allow the user to determine the number of applications of counterstain to be applied and to enter this number via the control panel keys prior to start of operation of the machine. Usually, it will be required to provide several additional applications of the counterstain solvent so the control means 51 will cause operation of the spray every four seconds (or other set or selectable time period) for the number of applications selected by the user. Thus, after the stop of the initial spray application, control means 51 will keep pump 47 energized. At four seconds after stop of the initial spray, i.e. after two complete revolutions of the carousel to allow the initial application of counterstain solvent to penetrate and decolorize and counterstain the specimen, control means 51 causes valve 45 to open to start spray again through nozzle 15. Valve 45 remains open for two seconds (the additional applications of counterstain solvent will usually be timed for one complete revolution of the carousel rather than the two revolutions of the initial application), providing an additional application of counterstain solvent will usually be timed for one complete revolution of the carousel rather than the two revolutions of the initial application), providing an additional application of counterstain solvent to each slide. At the end of the two second period, valve 45 is closed to immediately stop the spray. Additional applications of solvent are repeated every four seconds until the selected number of applications have been made. In some cases, it has been found desirable to increase the time between the later cycles to six or eight seconds, rather than four, seconds, to allow additional time for the decolorization and counterstain to be absorbed into the specimen. Usually no more than six applications of counterstain solvent will be desired.

After the desired number of applications of counterstain solvent, the carousel speed is increased for a three second period. The carousel is then slowed to the thirty RPM rate for an eight to fourteen second water wash, followed by a thirty second high speed cycle to dry the slides. The slides are then removed and examined. The apparatus is then ready to stain another batch of slides.

If specimens on the slides to be stained have not been fixed to the slides prior to the slides being loaded into the carousel, the specimens can be fixed to the slides by an initial application of the counterstain solvent or by an initial application of methanol. When the counterstain solvent is used to fix the specimens, upon start up of the apparatus, a four second spray of counterstain solvent is applied to the specimens in the same manner by pump 47, control valve 45, and nozzle 15, as described above. The carousel continues spinning at thirty RPM for twenty seconds to allow fixing of the specimens to take place. This is followed by a three second high speed spin and then a ten second water wash. This is followed by the normal staining cycle described above starting wtih the application of the crystal violet reagent. However, more crystal violet reagent is used to compensate for the decolorizer that was initially applied to the specimens during fixing. Thus, crystal violet is applied for fifteen seconds, followed by a fifteen second wait and a three second high speed spin and then an eight second application of crystal violet. This is followed by a fifteen second wash and then a three second high speed spin. The iodine is then applied and the remaining steps are as described above.

When the apparatus is not going to be used for a period of time, such as overnight, it is usually desirable to rinse all reagent nozzles. In order to do this, pump 68 is energized to pump water to manifold 70 and wash valves 43, 64, and 78 are operated to open the normally closed inlet. This allows water to flow from manifold 70 through tubing 80 to valve 43, and through tubing 42 and nozzle 15 to rinse it. Similarly, water flows through tubing 81 to valve 64 and through tubing 65 and nozzle 16, and through tubing 82 to valve 78 and through tubing 79 and nozzle 17. After the wash cycle described, it is necessary to reprime the system before staining operations begin again.

It has been found that methanol works well as a fixative and is better than water for rinsing the system. Thus, methanol can be substituted for the counterstain solvent in initially fixing the specimens and for water in cleaning the nozzles and system. However, water is still needed for the water rinses described during actual staining. Therefore, to implement the methanol fixing and rinsing, it is necessary to add another reagent reservoir, pump, valve, and nozzle.

In order to ensure that the spraying during critical reagent spraying through nozzle 15 starts immediately upon opening of control valve 47 and stops immediately upon closing of control valve 47, it is necessary to ensure that the flow line between the valve and nozzle remains full of fluid between cycles and that any compressible material, such as air pockets or expandable tubing, be eliminated from the line, or that any pressure build up in the line during spraying because of these factors be immediately released upon closing of the valve.

In the embodiment show in FIGS. 2 and 3, valve 45 has normally open and normally closed inputs. As previously described, the output from pump 47 is connected by tubing 46 to the normally closed input of valve 45. Thus, valve 45 must e opened to allow flow of fluid from the pump to the nozzle. The normally open input of valve 45 is connected through tubing 83 back to the supply line 48 from fluid supply bottle or reservoir 49 which is at substantially atmospheric pressure. Thus, line 83 serves as a vent. Immediately upon closing of valve 45 to stop the flow of fluid from pump 47 to nozzle 15, the flow tubing between valve 45 and nozzle 15 is vented to atmospheric pressure through the normally open input of valve 45 and tubing 83. This immediately provides relief for any pressure build up in the line. With this relief, however, it is necessary to provide a check valve in the line to stop back flow of fluid form the nozzle which would empty the nozzle and flow lines of fluid.

Figure 4:
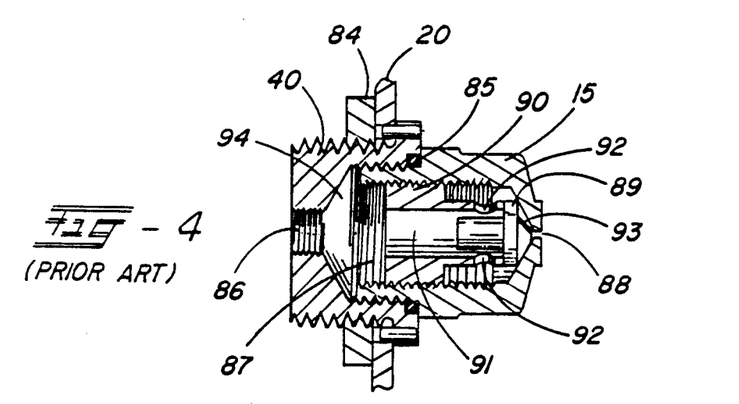
FIG. 4, a longitudinal vertical section through a nozzle showing a prior art nozzle configuration.

The normal nozzle used with the prior art apparatus discussed is shown in FIG. 4 and includes the nozzle 15 threaded into nozzle holder 40. Nozzle holder 40 is mounted in an opening in spray chamber side wall 20 and is secured therein by a nut 84. An O-ring 85 seals the connection between the nozzle 15 and nozzle holder 40. A threaded opening 86 accepts hose connector 41. Within the central bore 87 of nozzle 15, against nozzle spray opening 88, is a spray-forming member 89. Spray-forming member 89 is held in place by threaded member 90 with central bore 91 therein. Radial openings 92 extend through member 90 toward its forward end. The forward surface of spray-forming member 89 which rests against the forward closed end of nozzle bore 87 has grooves 93 therein for passage of fluid to nozzle opening 88.

In use, fluid to be sprayed is introduced under pressure through opening 86 in nozzle holder 40 and flows into larger opening 94 of the nozzle holder 40 and into bore 87 of nozzle 15. The fluid flows through central bore 91 in threaded member 90 through radial openings 92 therein, around the outside of the forward ends of members 90 and 91 and through passages 93 to nozzle outlet 88. This prior art nozzle arrangement works well where spray control is not critical, however, the extra area in the back of nozzle bore 87 and in holder opening 94 generally will have air therein and during spraying, the fluid will compress the air and partially fill the space wtih fluid. In the actual equipment, this space is about 1 ml, and, under normal operating conditions, about one-third to one-half of the space is filled with air. When spraying ceases, the air trapped therein, which has been compressed, will expand and force some of the fluid therein out through the nozzle. This produces an undesirable afterspray.

Figure 5:
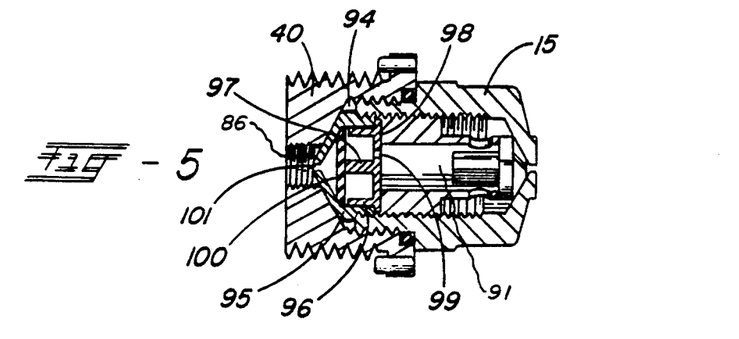
FIG. 5, a longitudinal vertical section similar to that of FIG. 4, but showing a check valve of the invention therein.
Figure 6:
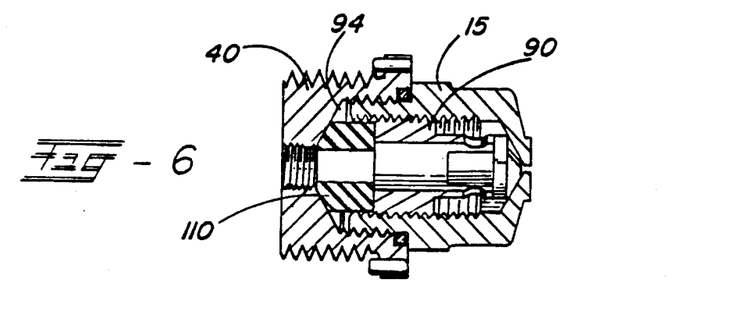
FIG. 6, a longitudinal section similar to that of FIG. 4, but showing an inset of the invention therein.
Figure 7:
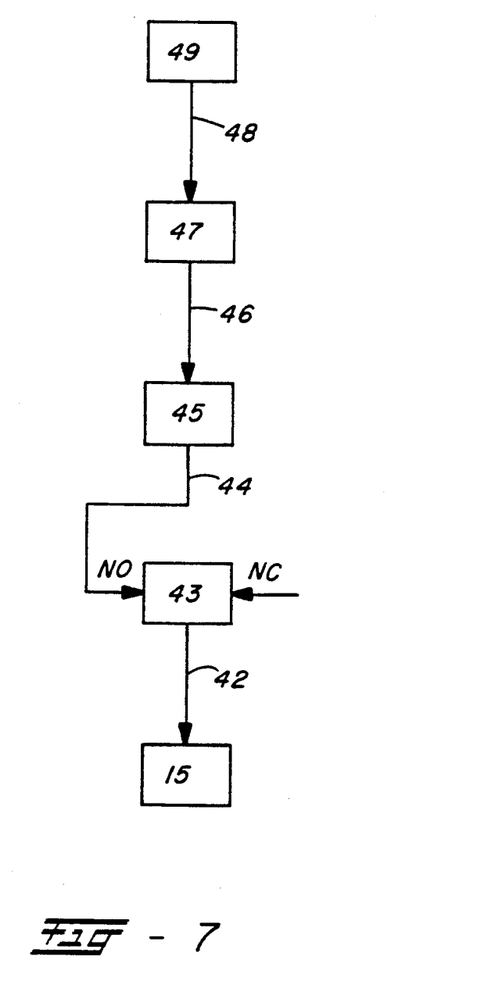
FIG. 7, a flow diagram similar to that of FIG. 3, but only showing the left-hand side thereof and showing a slightly different embodiment.

FIG. 5 shows the same nozzle arrangement but includes a check valve of the invention therein to prevent back flow of the fluid from the nozzle and to eliminate the extra air and fluid space in the nozzle holder and nozzle. The check valve includes a valve body 95 with a threaded end to screw into threaded bore 87 of nozzle 15 and an opposite end which fits into nozzle holder opening 94. A hollow cylindrical insert 96 slides into check valve body 95 and has a central shaft 97 extending from insert end 98. A series of openings 99 extend through end 98. A resilient disc 100 is positioned in valve body 95 with its center against shaft 97. In operation, pressurized fluid passes from nozzle holder opening 86, through opening 101 in check valve body 95, around the outer edges of disc 100, which are displaced thereby to allow fluid flow there around, through the open areas of valve insert 96, and through openings 99 in insert end 98 into bore 91 in member 90. When flow of pressurized fluid stops, any reverse flow causes disc 100 to seal against the inside end of valve body 95 to seal opening 101 and prevent any reverse flow. An alternate embodiment is shown in FIGS. 6 and 7. In this embodiment, valve 45, FIG. 7, does not have a normally open input, or, the normally open input is sealed. Thus, no venting of the fluid tubing takes place. Steps must be taken to substantially eliminate any sources of pressure in the line so that the spray will stop upon closing of valve 45. Thus, the tubing used should not stretch under the pressure used and the air and fluid areas in the nozzle holder and nozzle should be blocked. For this purpose, it has been found that a length of silicone tubing 110, FIG. 6, can be placed between the nozzle member 15 and the base of nozzle holder opening 94. The silicone tubing compresses to form a seal against nozzle holder 40 and nozzle member 92 and closes the air and fluid space otherwise available. It has been found that with this arrangement, spray stops upon closing of the valve 45. Since valve 45 does not vent upon closing, there is no need for a check valve at the nozzle. Closed valve 45 prevents any back flow of fluid from the nozzle. With either embodiment, valve 45 can be located anywhere in the line between pump 47 and nozzle 15. It can be on either side of valve 43.

Figure 8:
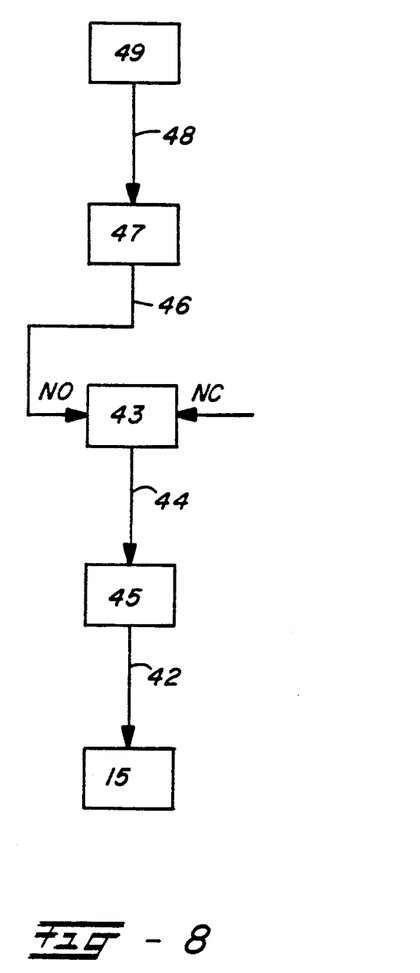
FIG. 8, a flow diagram similar to that of FIG. 7, but showing the valves in different order.
Figure 9:
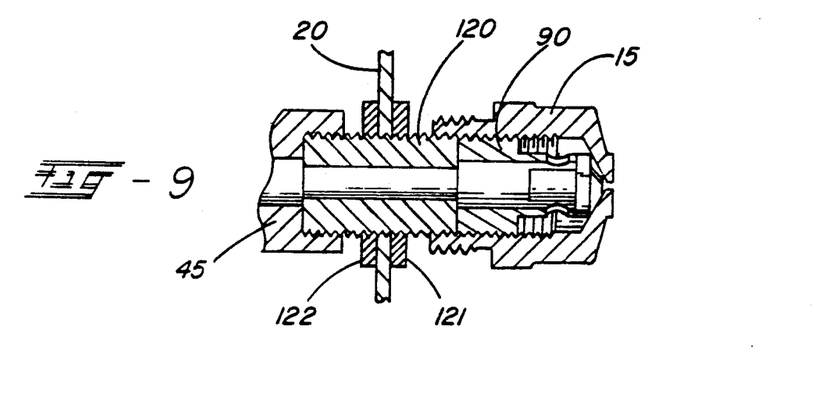
FIG. 9, a longitudinal section through another embodiment of a nozzle of the invention.

FIGS. 8 and 9 show a further alternate embodiment. In the embodiment of FIG. 8, valve 45 again does not have a normally open inlet port or the normally open inlet port is sealed. Again, there is no venting. In this embodiment, valve 45 is shown between valve 43 and nozzle 15 and is preferably located as close to nozzle 15 as possible to reduce the amount of flow line between the valve and nozzle.

FIG. 9 shows an arrangement for mounting valve 45 closely adjacent to nozzle 15. In this embodiment, nozzle 15 is threaded onto a nipple 120. Nipple 120 passes through spray chamber side wall 20 and is held in place by nuts 121 and 122 threaded onto nipple 120 and tightened against the opposite sides of wall 20. This mounts nozzle 15 in the spray chamber. It should also be noted that the nipple 120 provides a small flow passage into the valve and does not leave any air space at the back of the valve. Valve 45, shown only partially in FIG. 9, is mounted directly to nipple 120, thus providing a very short flow passage between the valve and nozzle 15. In this embodiment, valve 45 also acts as the check valve to prevent back flow of fluid from the nozzle.

While the carousel is configured to hold a plurality of slides, the embodiment shown holds twelve slides, any number of slides up to the full number of slides can be stained at any time. Thus, the apparatus can be operated to stain a single slide which may be placed in the carousel. However, when only a single slide is stained, or any number of slides less than a full carousel are stained, the apparatus as described above for gram staining, or the prior art apparatus used for hematology staining, operates as if the carousel was full. With only several slides in the carousel, such operation wastes reagents and in some cases it would be desirable to control reagent spray so that the spray occurs only during the time the slides in the carousel are passing by a nozzle. Such controlled operation was difficult wit the prior art apparatus, which merely activated the pump to start the spray, since the afterspray would usually continue through about an additional half revolution of the carousel so the potential savings of reagent by stopping the pump sooner for a partially loaded carousel then for a fully loaded carousel was not significant. However, with the control system of the present invention, which allows the accurate on-off control of the spray of reagent, in some cases it becomes worthwhile to control the spray of such reagent for the specific number of slides actually in the carousel. For such control, upon the start of operation of the apparatus, the user indicates the number of slides in the carousel via the control panel. The control means then operates the control valve to start the spray of reagent just prior to the slide or slides passing the nozzle and stops spray just after passage of the slide or slides by the nozzle. In loading the carousel with less than a full load of slides, to keep the carousel balanced, the slides should be loaded opposite one another. Thus, if two slides are being stained, the two slides would be located in the carousel opposite one another, i.e., one slide would be in position one and one slide in position seven. This would position the two slides, for example, as shown in FIG. 2. Additional slides would be added adjacent to the opposite slides so two ore slides would take positions two and eight, respectively. Further, positions in the carousel will generally be labeled and for individual slide staining, the slides should always be placed in the first labeled space first, followed by the second labeled space, etc. This is because the apparatus will assume such positions for spraying when a number less than all slides needed to fill the carousel is specified.

The control means may be as simple or complex as desired and will usually take the form of electronic timing and control circuitry to operate and control the time of operation of the various pumps and valves. For more complex control, the control circuitry may include a microprocessor programmed to operate the apparatus in certain ways in response to input signals from the control panel, or may be custom programmed by the user via the control panel.

Figure 10:
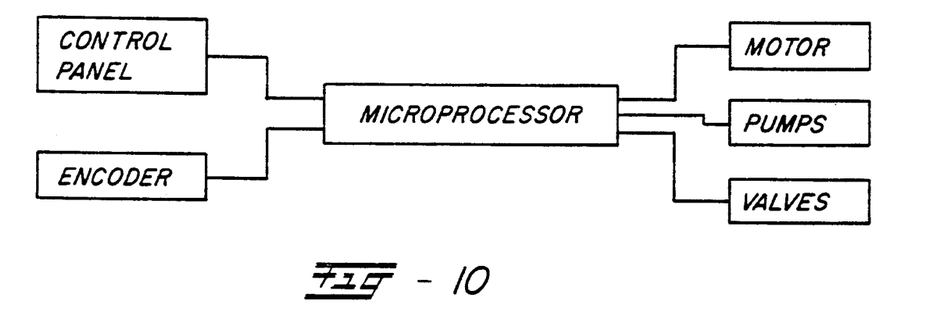
FIG. 10, a block diagram of a control system of the invention.

FIG. 10 is a block diagram of a basic microprocessor control means for the invention. The control panel as shown in FIG. 1 comprises six buttons 147-152 representing "clean", "stop", "run", "program", "time check", and "cytocent" functions, respectively, and ten numbered push-buttons 153 for entering numbers. A display 154 displays instructions entered or other information supplied by the microprocessor. The control panel block in FIG. 10 provides information to the microprocessor or receives information from the microprocessor to be displayed.

An encoder 155 is coupled to shaft 22 in motor 37, FIG. 2, and is shown by a block feeding into the microprocessor in FIG. 10. The encoder provides signals to the microprocessor indicative of the position and speed of rotation of shaft 22. Various encoders may be used but an encoder that provides two separate outputs, one providing 500 pulses per revolution and the other providing two pulses per revolution, one pulse for each 180° of rotation of the shaft, has been found to be especially satisfactory. The encoder is used to measure motor speed so speed can be accurately controlled by the microprocessor, this being the basic function if individual slide staining control is not provided, and to indicate position of the carousel with respect to the nozzles if individual slide staining control is provided. With the individual slide staining control, the 500 pulses per revolution is divided into twelve sets of pulses representing twelve corridors or time periods representing each of the individual slides in the carousel. Thus, the microprocessor can keep track of the position of the individual slides and activate the nozzles to spray the appropriate number of individual slides. The pulses provided for each half revolution are used to keep track of half or full revolutions and to correct for the fact that the 500 pulses do not evenly divide into the twelve corridors.

The microprocessor provides signals to the motor, the pumps, and the valves to operate them at the appropriate times. The individual pumps and valves are shown collectively by respective blocks in FIG. 10. Thus, the block labeled "Pumps" may have four individual pumps as shown in the embodiment described, or any other number of pumps appropriate for a particular embodiment.

While various microprocessors can be used, a Motorola 68HC11 has been found satisfactory. The various interfaces for inputs and outputs to the microprocessor are not shown, but would be obvious to a person skilled in the art.

Since it will usually be desirable to be able to load the carousel onto receiving hub 22a in several positions, rather than having to line up only a single position, it will be advantageous to provide the apparatus with sensing means to sense the starting or first position for slides in the carousel. For this purpose, the carousel may include a pair of magnets 160, FIG. 1, embedded therein at opposite sides of the carousel (a pair is preferred to keep the carousel balanced). A sensor 161, such as a Hall effect sensor or a magnetoresistive magnetic sensor as made by Micro Switch, the latter sensor being identified as a series SS2 digital position sensor, which provides an electrical output pulse each time a magnet passes, is mounted on the side of the spray chamber. The sensor will be electrically connected to the control means to provide its output pulses to the control means. The pulses from the sensor will indicate the position of the carousel and indicate to the control means when to start spraying in order to spray the particular slide positions in the carousel which are actually occupied by slides. The length of the spray necessary to spray the slides present in the carousel will be determined by the control means based upon entry by the user through the control panel controls of the number of slides in the carousel. The length of spray is measured by counting the pulses from the motor encoder 155. The delay time between sensing the magnetic pulse and start of spray for a particular nozzle (the nozzles are located at different positions in the spray chamber with respect to the sensor), is programmed into the control means. Again, the delay time is measured by, or the positions of the sensed slides in the carousel are monitored by, tracking of the pulses from the motor encoder.

Figure 11:
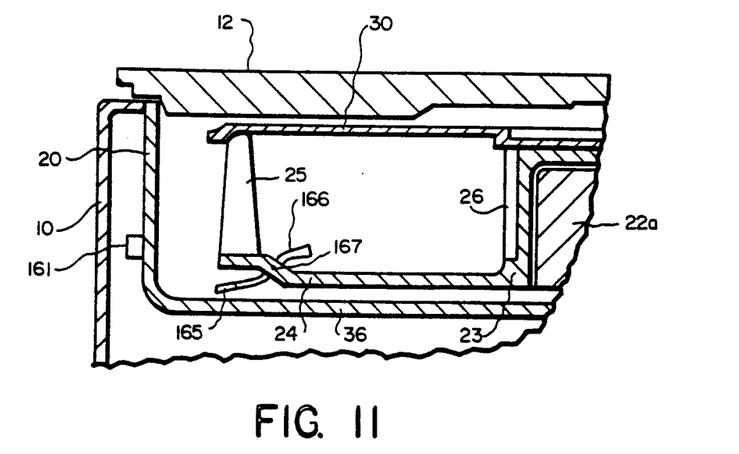
FIG. 11, a fragmentary section through a portion of the spray chamber and carousel showing a movable magnet and no microscope slide in position in the carousel.
Figure 12:
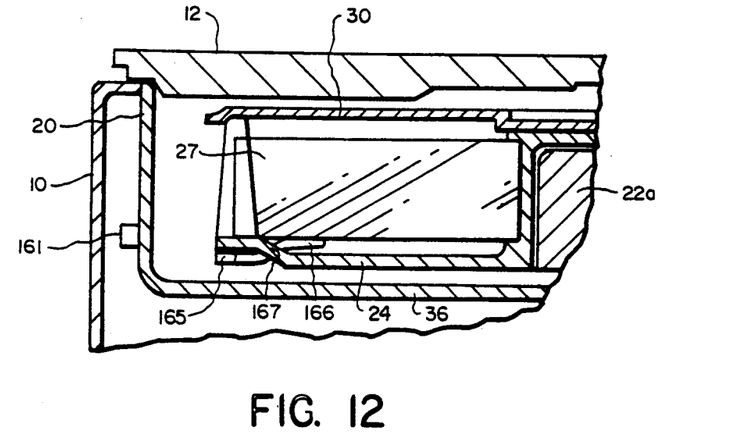
FIG. 12, a fragmentary section similar to that of FIG. 11, but showing a slide in position in the carousel.

While merely keeping track of the position of the carousel and positioning the slides therein in predetermined positions with respect to the carousel so that the position of the slides is known works satisfactorily and will be used in most presently contemplated applications because of its reliability, it may be desirable in some instances to provide for individual slide sensing. This would allow a user to place the slides in a carousel as the user desired without having to start at a predetermined first position. FIGS. 11 and 12 show construction of a carousel having individual magnets 165 secured to arms 166 pivotally mounted by pins 167 on carousel bottom portion 24 so as to be in a lowered position when no slide is present above the magnet, FIG. 11, but to be moved to raised position by a slide being positioned in the carousel above the magnet, FIG. 12. An arm is associated wtih each slide position in the carousel and is moved when a slide is placed in and held by the carousel in the associated position. Sensor 161 is located to be activated by any magnet in raised position, indicating the presence of a slide, but not to be activated by a magnet in lowered position.

Rather than a magnetic sensor, a capacitive proximity sensor such as a Omron E2K-C sensor capable of sensing passage of glass or an ultrasonic sensor made by Megatron Corp. could be used to sense passage of the glass slides by a sensor location.

Figure 13:
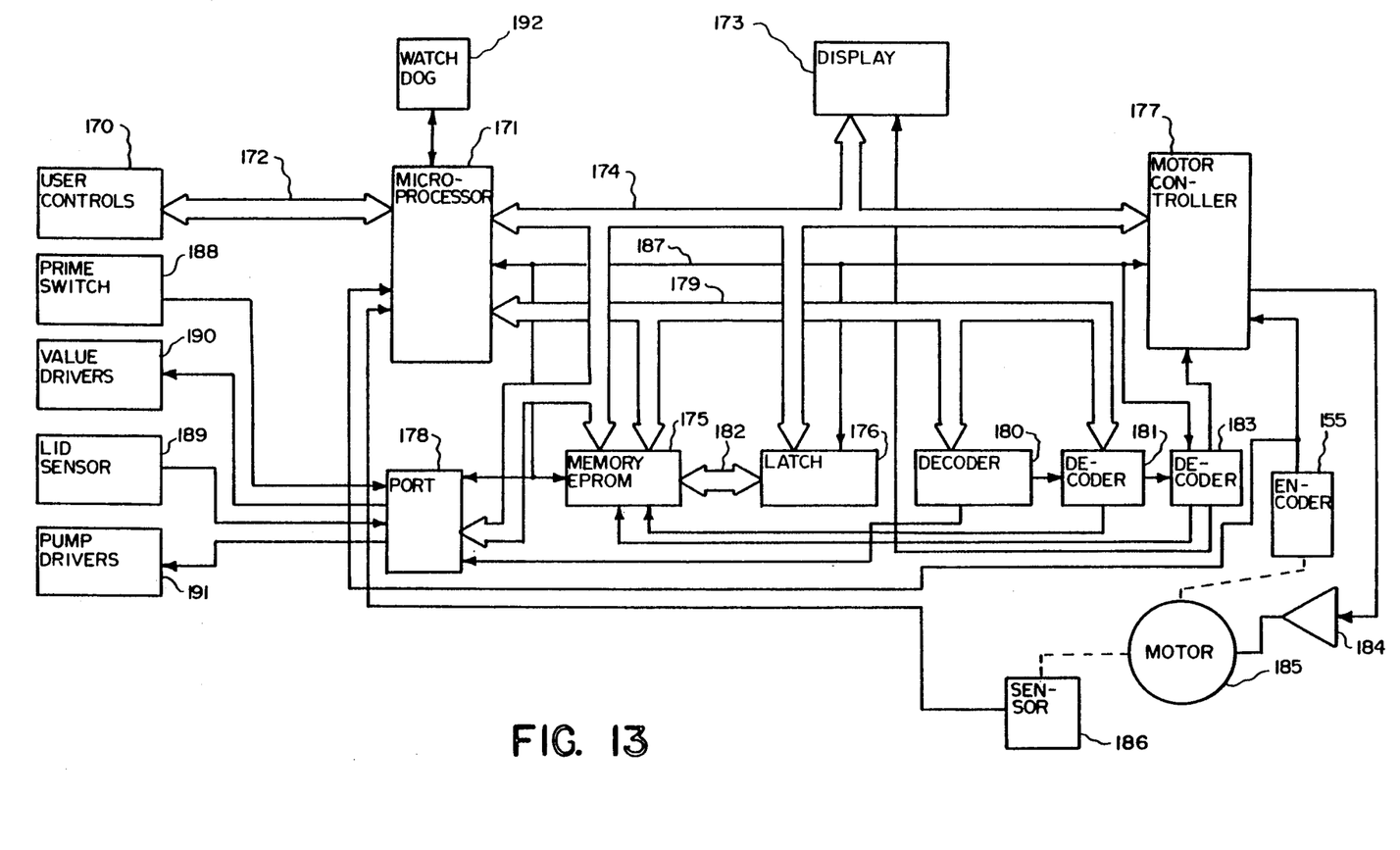
FIG. 13, a more detailed block diagram of a control system of the invention.

A more detailed block diagram of the control means is provided in FIG. 13. The various switches of the control panel 11, FIG. 1, are indicated in FIG. 13 a user controls block 170 and are connected to microprocessor 171 through interface bus 172. The display 154 of the control panel is indicated by display block 173 and is connected to microprocessor 171 through data bus 174. The microprocessor is connected to a memory chip 175, such as an erasable programmable read only memory (EPROM) through data bus 174. The EPROM memory is used to store the program to operate the apparatus. The microprocessor is also connected through data bus 174 to latch 176, motor controller 177, and to parallel port 178. The microprocessor 171 is connected through address bus 179 to memory 175, to decoder 180, and to decoder 181.

Latch 176 may be a 74HC573 chip and supplies addressing information form the data bus through address bus 182 to the memory 175. Decoder 180 may be a 74HC138 chip and is used to decode address information and provide signals through parallel port 178 and decoder 181 to operate selected components. Decoder 181, along with decoder 183, may be 74HC139 chips and are used to decode address information and provide signals to the motor controller 177, display 173, and memory 175 to indicate when to accept and send data.

Motor Controller 177 may be a HCTL-1000 chip made by Hewlett Packard and provides drive signals through power amplifier 184 to motor 185 to cause operation of the motor at desired times and speeds. Motor encoder 155, such as a HEDS-5500 optical encoder provides the 500 pulses per revolution of the motor shaft and separately, two pulses per revolution of the motor shaft. The output signals from the encoder are supplied to motor controller 177 and microprocessor 171. Sensor 186 is the sensor, such as magnetic sensor 161, FIG. 2, which senses the position of the carousel. Signals from sensor 186 are connected to microprocessor 171. Line 187 is a control line which provides clock signals to the circuitry.

External control signals from a prime switch 188, indicating that a pump should be run to prime its associated system, and signals from the lid sensor 189 indicating that the motor should not operate if the top 12 of the apparatus is open, are connected to port 178, such as a MC146823 parallel port chip, and provide their signals through port 178 and data bus 174 to microprocessor 171. Output signals to operate the various valves are provided by microprocessor 171 through data bus 174 and port 178 to valve drivers 190. Similarly, output signals to operate the various pumps are provided by microprocessor 171 through data bus 174 and port 178 to pump drivers 191. It should be noted that the blocks labeled valve drivers and pump drivers contain a number of individual driver circuits so that each individual valve or pump in a system can be separately operated. A watch dog chip 192 such as a 1232 chip, monitors power to the circuitry and resets the processor during power transients or periods of low voltage.

Figure 14:
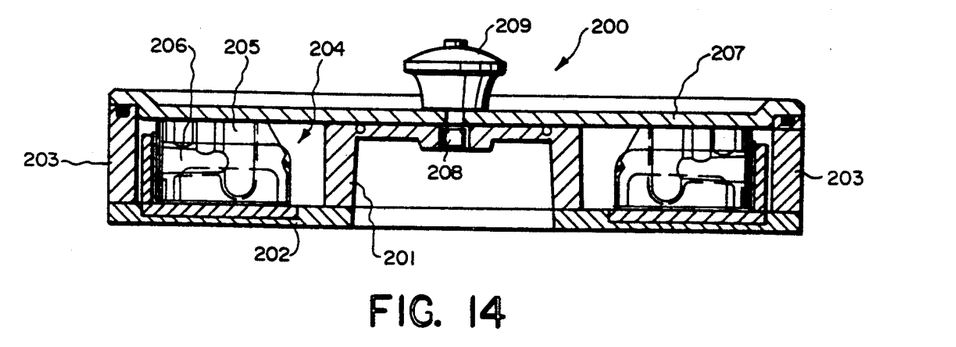
FIG. 14, a vertical section of a centrifuging rotor usable with the invention.

The apparatus of the invention may also be used to perform centrifuging operations. For this purpose a centrifuging rotor is placed in the apparatus in place of the carousel 21. For example, a centrifuging rotor 200, FIG. 14, specifically designed for cytocentrifuging tests, and having a central hub portion 201 configured to be positioned in the spray chamber over hub 22a, FIG. 1, in similar manner as carousel 21 is positioned in the spray chamber, may be positioned in spray chamber 14 over hub 22a when it is desired to perform cytocentrifuging tests. The specific construction of centrifuging rotor is not a part of this invention so is not set further in detail here. Generally, however, the rotor includes a bottom portion 202 and outer wall 203 secured thereto with sample chamber assembly 204 mounted thereon having a sample well 205 and connecting sample passage 206 therein. Upon rotation of the rotor, the sample is forced out of well 205, through passage 206 and onto a filter placed against outer wall 203. A cover 207 is positioned over the top of the rotor and the rotor is held in place by a bayonet latching mechanism 208 similar to latching mechanism 31 used for carousel cover 30. An enlarged head 209 serves as a handle for the rotor.

It will be understood that when using the centrifuging rotor, it is not desired to apply spray. Thus, the control panel 11 will include a push-button control 152 which will place the apparatus in centrifuging mode wherein the motor causes rotation of the centrifuge rotor 200 at desired speed for desired time as set through buttons 153 either directly or as coded and retrieved from the apparatus memory. No spray will occur during centrifuging. As a safety precaution, when sensor 161, FIG. 2 or 186, FIG. 13, is used, the centrifuging rotor will not contain magnets 160 so there will be no signal picked up by the sensor. Thus, if a spray setting is accidently set when the centrifuge rotor is in the apparatus, no signal from sensor 161 or 186 is generated and the control means will not activate the spray and, preferably, will stop operation of the motor and ask, through display 154 or other means, such as an alarm, that the apparatus be reset for the desired operation of the machine. If desired, various coding and sensing means could be used so that the apparatus can sense which type of rotor has been placed in the spray chamber. With such coding, the apparatus can automatically set itself for proper operation for the carousel or rotor used. If only spray carousels and centrifuging rotors are to be used, the presence of magnets in the carousel and lack of magnets in the rotor can be used by the control means to make that determination. If desired, in addition to magnets 160, FIG. 2, which, in conjunction with sensor 161, determine the position of the carousel in the spray chamber, a continuous magnetic strip could encircle a portion of the bottom of the carousel with a sensor, such as a reed switch or other magnetic sensor, positioned to provide a signal whenever the carousel is placed in the spray chamber regardless of its angular position. The centrifuging rotor would not provide such signal. Alternately, the centrifuging rotor could have the continuous magnetic strip positioned to activate sensors not activated by the carousel. In either instance, the particular nature of the item placed on hub **22*a* can be determined by the apparatus and the apparatus set to operate accordingly. Rather than magnetic actuators and sensors, a number of other identification means could be used so that the apparatus can recognize and determine the nature of the item placed on hub 22*a*** and automatically set itself for proper operation.

Various different test procedures requiring spinning of a sample or in which spinning of a test device may be desireable or advantageous may be carried out by the apparatus of the invention by merely configuring a rotatable element, such as a rotor or carousel as described, to fit into the spray chamber of the apparatus and perform the desired procedure, and by programming the apparatus to perform in the desired manner. The hub **22*a*** forms a rotation means to receive the rotatable element to be placed for rotation in the spray chamber. While a hub has been shown, the rotation means could take various other forms such as a platform to which the rotatable element can be secured for rotation therewith. As described above, various identification means can be provided on or in association with the rotatable element, such as the magnets or magnetic strip specifically described, which, in cooperation with a sensor means associated wtih the control means, produces signals (which may be the lack of signals) which identify the particular rotatable element or type of rotatable element and cause the control means to operate the apparatus in a desired or appropriate manner for that rotatable element. For example, such desired or appropriate control or operation would be providing desired reagent spray for a slide staining carousel and ensuring that no spray of reagent occurs during rotation of a centrifuge rotor. Specific time and duration of rotation or of supply of various reagent sprays can also be responsive to the specific identification of the rotatable element.

Various staining procedures may be carried out with the apparatus including the gram staining described, as well as, for example, hematology, cytology, and papiniculo staining. For staining, various reagents may be used with the equipment. For the gram staining described, it has been found that a counterstain solvent made up of 60% isopropanol, 40% methanol, and 2.5 gram/liter safranin works well.

Also, while only the reagent line for the counterstain solvent has been shown and described with the valve for accurate control of the spray, similar control valves and nozzle and flow line configurations can be on any of the other reagent lines or all of the other reagent lines. Where the apparatus is adapted to control the spray for less than a full carousel load of slides, i.e. to control the spray so that reagent is sprayed only during the time a slide is in position to receive the sprayed reagent, all reagent liens will preferably have a control valve.

While the invention has been described in connection with gram staining and certain modes of operation have been described in detail, it should be realized that the various spray times, rate of rotation of the carousel, and even the sequence of some of the steps may be varied for the gram staining, and that various other types of staining can be performed using the apparatus with varying reagents and steps.

Whereas this invention is here illustrated and described with specific reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A method for gram staining bacterial specimens on slides using automatic staining equipment including carousel means for holding a plurality of slides having bacterial specimens thereon to be stained, means for rotating the carousel means at predetermined speeds in the spray chamber, and means for directing and controlling spray of reagents onto the slides and specimens during rotation of the carousel means, comprising directing a spray of crystal violet reagent onto the slides in the carousel in the spray chamber so as to saturate the bacterial specimens on the slides with crystal violet reagent; directing a spray of water onto the slides in the carousel in the spray chamber to rinse crystal violet reagent from the slides; directing a spray of iodine reagent onto the slides in the carousel in the spray chamber so as to saturate the bacterial specimen on the slides with iodine reagent; directing a spray of water onto the slides in the carousel in the spray chamber to rinse iodine reagent from the slides; directing a spray of a mixture reagent which is a mixture of decolorization solvent and counterstain onto the slides in the carousel int eh spray chamber and accurately controlling the amount of mixture reagent that is applied to the slides so that a desired amount of mixture reagent is accurately applied to each slide in the carousel; and directing a spray of water onto the slides in the carousel in the spray chamber so as to rinse the mixture reagent from the slides.

2. A method for gram staining according to claim 1, including providing a time delay between the application of reagent and the application of the water following application of the reagent to provide time for the reagent to act on and be absorbed by the bacterial specimen.

3. A method for gram staining according to claim 2, wherein the speed of rotation of the carousel is increased for a set time period between application of a reagent and application of water following application of the reagent for selected reagent applications.

4. Apparatus for applying a controlled amount of reagent to a microscope slide, comprising a spray chamber; carousel means for holding a plurality of slides to be sprayed and rotatably mounted in the spray chamber; nozzle means located int he spray chamber adjacent a portion of the carousel means for directing spray of reagent toward the slides held in the portion of the carousel means adjacent the nozzle means; means for rotating the carousel means at predetermined speeds in the spray chamber so as to move the slides mounted in the carousel means pst the nozzle means; reagent reservoir means for storing a supply of reagent; pump means for pumping reagent from said reservoir means to said nozzle means; flow line means extending between said pump means and said nozzle means through which reagent can flow between said pump means and nozzle means; control valve means to control flow of reagent between said pump means and said nozzle means; means to determine and monitor the angular position of the carousel means in the spray chamber; and control means responsive to the means to determine and monitor the angular position of the carousel means to coordinate operation of said pump means, valve means, and carousel means to accurately cause spray of reagent during predetermined known passage of the carousel means past the nozzle means whereby spray of reagent onto the slides is accurately controlled as the slides pass the nozzle means.

5. Apparatus for applying a controlled amount of reagent to a microscope slide according to claim 4, wherein the means for rotating the carousel means is an electric motor having a shaft which rotates to cause rotation of the carousel, and wherein the means to determine and monitor the angular position of the carousel means includes an encoder coupled to the motor shaft for producing output pulses indicative of shaft rotation.

6. Apparatus for applying a controlled amount of reagent to a microscope slide according to claim 5, wherein the encoder provides two sets of output pulses, each set producing a different number of pulses for each rotation of the shaft.

7. Apparatus for applying a controlled amount of reagent to a microscope slide according to claim 5, wherein the means to determine and monitor the angular position of the carousel means additionally includes sensor means positioned to sense passage of predetermined portions of the carousel means as it rotates in the spray chamber and to produce signals indicative of passage of said predetermined portions passing the sensor means.

8. Apparatus for applying a controlled amount of reagent to a microscope slide according to claim 7, wherein the sensor means is adapted to sense a magnetic field and wherein the carousel means includes at least one magnet therein positioned to activate the sensor as the portion of the carousel means wtih the magnet therein rotates passed the sensor.

9. Apparatus for applying a controlled amount of reagent to a microscope slide according to claim 8, wherein a pair of magnets is mounted in the carousel means, each magnet of the pair being at diametrically opposed sides of the carousel means.

10. Apparatus for applying a controlled amount of reagent to a microscope slide according to claim 9, wherein the control means will not allow spray of reagent unless signals are received from the sensor.

11. Apparatus for applying a controlled amount of reagent to a microscope slide according to claim 8, wherein the portions of the carousel means to be sensed are portions wherein slides are located, wherein the sensor means is adapted to sense a magnetic field, and wherein a separate magnet is movably mounted at each location where a slide may be held in the carousel means so that the magnet will move to a first position when no slide is held by that location of the carousel means, and will move to a second position when a slide is held by that location of the carousel means, the magnet in the second position causing activation of the sensor when the magnet passes the sensor.

12. Apparatus for applying a controlled amount of reagent to a microscope slide, comprising a spray chamber; rotation means for receiving a rotatable element to be rotated in the spray chamber; a plurality of rotatable elements, each rotatable element of the plurality being received by the rotation means at a selected time for a selected different operation of the apparatus, at least one of said plurality of elements being carousel means for holding a plurality of slides to be sprayed; nozzle means located int he spray chamber for directing spray of reagent into the chamber and toward slides held in a portion of a carousel means adjacent the nozzle means when the carousel means is received by the rotation means; means for rotating the rotation means at predetermined speeds in the spray chamber so as to move a rotatable element received by the rotation means past the nozzle means; reagent reservoir means for storing a supply of reagent; supply means for controllably supplying reagent from said reservoir means to said nozzle means to be sprayed therefrom at desired times; means to determine and monitor the angular position of the rotation means in the spray chamber; and control means responsive to the means to determine and monitor the angular position of the rotation means to coordinate and cause desired operation of said supply means and said means for rotating the rotation means for the rotatable element received by the rotation means in the spray chamber.

13. Apparatus for applying a controlled amount of reagent to a microscope slide according to claim 12, wherein rotatable elements to be received by the rotation means include identification means, and wherein the control means has associated sensor means to cooperate wtih the identification means of a rotable element whereby the control means can identify the rotatable element and cause desired operation of the supply means and rotation means.

14. Apparatus for applying a controlled amount of reagent to a microscope slide according to claim 13, wherein the operation of the supply means by the control means is responsive to the sensor means.

15. Apparatus for applying a controlled amount of reagent to a microscope slide according to claim 14, wherein the control means will operate the supply means to cause spray of reagent only upon sensing by the sensor of certain identification means.

* * * * *